Figure 1:
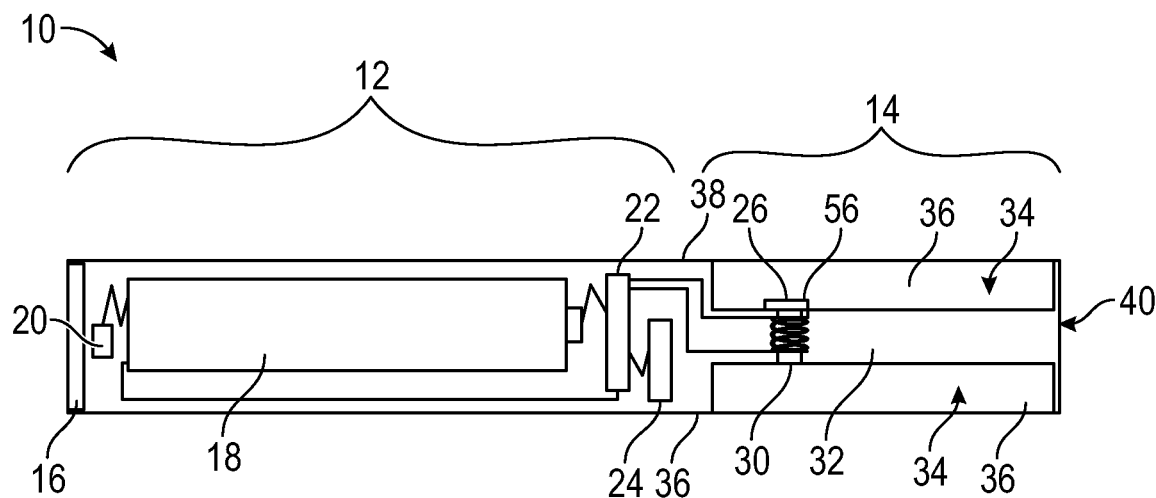

US012168094B2

(12) United States Patent
Hon et al.

(10) Patent No.: US 12,168,094 B2
(45) Date of Patent: Dec. 17, 2024

(54) HIGH FREQUENCY POLARIZATION AEROSOL GENERATOR

(71) Applicant: FONTEM VENTURES B.V., Amsterdam (NL)

(72) Inventors: Lik Hon, Beijing (CN); Zhuoran Li, Beijing (CN)

(73) Assignee: FONTEM VENTURES B.V., Amsterdam (NL)

( * ) Notice: Subject to any disclaimer, the term of this patent is extended or adjusted under 35 U.S.C. 154(b) by 0 days.

(21) Appl. No.: 17/874,059

(22) Filed: Jul. 26, 2022

(65) Prior Publication Data

US 2024/0032600 A1 Feb. 1, 2024

Related U.S. Application Data

(63) Continuation of application No. 16/074,760, filed as application No. PCT/CN2016/074334 on Feb. 23, 2016, now abandoned.

(51) Int. Cl.
*A24F 40/46* (2020.01)
*A24F 40/10* (2020.01)
(Continued)

(52) U.S. Cl.
CPC ............ *A61M 15/06* (2013.01); *A24F 40/42* (2020.01); *A24F 40/46* (2020.01); *A24F 40/50* (2020.01);
(Continued)

(58) Field of Classification Search
None
See application file for complete search history.

(56) References Cited

U.S. PATENT DOCUMENTS

| | | | | |
|---|---|---|---|---|
| 4,825,028 A * | 4/1989 | Smith | H05B 6/683 219/718 |
| 4,978,826 A * | 12/1990 | DeRuiter | H05B 6/54 99/451 |

(Continued)

FOREIGN PATENT DOCUMENTS

| | | |
|---|---|---|
| CN | 1541577 A | 11/2004 |
| CN | 101116542 A | 2/2008 |

(Continued)

OTHER PUBLICATIONS

European Patent Office, "Extended European Search Report" for European Application No. 16890969.5; Date of Mailing: Dec. 19, 2018; 8 pages.

(Continued)

*Primary Examiner* — Philip Y Louie
*Assistant Examiner* — Sonny V Nguyen
(74) *Attorney, Agent, or Firm* — Perkins Coie LLP; Kenneth H. Ohriner

(57) ABSTRACT

A vaporizing device such as an electronic cigarette includes a housing (11) containing a battery (12) or other electrical power source electrically connected to a high frequency oscillation circuit (50). Two electrodes or electrode pads (56) with a liquid space (70) between them are electrically connected to the high frequency oscillation circuit (50). A liquid supply (34) in the C housing (11) provides a liquid into the liquid space (70). The high frequency oscillation circuit (50) is switched on by a manual switch or by a sensor (24) sensing inhalation by a user. The liquid is vaporized by dielectric heating.

13 Claims, 6 Drawing Sheets

(51) Int. Cl.
*A24F 40/42* (2020.01)
*A24F 40/50* (2020.01)
*A61M 15/00* (2006.01)
*A61M 15/06* (2006.01)
*H05B 6/62* (2006.01)

(52) U.S. Cl.
CPC .......... *A61M 15/0001* (2014.02); *H05B 6/62* (2013.01); *A24F 40/10* (2020.01); *A61M 2205/8206* (2013.01)

(56) References Cited

U.S. PATENT DOCUMENTS

| | | |
|---|---|---|
| 6,246,040 B1 | 6/2001 | Gunn |
| 2006/0196518 A1 | 9/2006 | Hon |
| 2009/0283103 A1 | 11/2009 | Nielsen et al. |
| 2010/0200008 A1 | 8/2010 | Taieb |
| 2011/0139773 A1 | 6/2011 | Fagrell et al. |
| 2011/0277764 A1 | 11/2011 | Terry et al. |
| 2012/0090630 A1 | 4/2012 | Hon |
| 2012/0234315 A1 | 9/2012 | Li et al. |
| 2015/0040925 A1 | 2/2015 | Saleem et al. |
| 2015/0164142 A1 | 6/2015 | Li et al. |
| 2015/0216237 A1 | 8/2015 | Wensley et al. |
| 2017/0112193 A1 | 4/2017 | Chen |
| 2017/0164655 A1* | 6/2017 | Chen ........................ A24F 40/46 |
| 2017/0231278 A1 | 8/2017 | Mironov et al. |
| 2018/0064169 A1* | 3/2018 | Biel ........................ A24F 40/44 |
| 2019/0356047 A1 | 11/2019 | Guduru |

FOREIGN PATENT DOCUMENTS

| | | | |
|---|---|---|---|
| CN | 201072979 Y | | 6/2008 |
| CN | 201076006 Y | | 6/2008 |
| CN | 201238610 Y | | 5/2009 |
| CN | 100593982 C | * | 3/2010 |
| CN | 103720055 A | | 4/2014 |
| CN | 204070580 U | | 1/2015 |
| EP | 3406148 A1 | | 11/2018 |
| TW | 1320698 B | | 2/2010 |
| WO | 9920940 A1 | | 4/1999 |

OTHER PUBLICATIONS

Fischer, U., et al., "Carbon Aerogels as Electrode Material in Supercapacitors", Journal of Porous Materials, 4, 281-285 (1997).
IP Office China, "Decision of Rejection", for Application No. 201680082400.9, Mail Date: Dec. 3, 2020, 22 pages.
IP Office China, "First Office Action", for Chinese Application No. 201680082400.9, Mail Date: Apr. 28, 2020 with English summary, 11 pages.
IP Office China, "Second Office Action", for Application No. 201680082400.9, Mail Date: Sep. 11, 2020, 5 pages.
Liu, "Machine translation of CN 100593982", translated Jul. 1, 2021, Espacenet.com (2021).
Nawsheen, Sabia, et al., "Impact of Nicotine Consumption on Hyper Acidic Patients Taking PPI: An In-Vitro and Computational Analysis", Health, 11, 129-141 (2019).
State Intellectual Property, Office, PRC China, "International Search Report and Written Opinion", for PCT/CN2016/074334, Oct. 10, 2016, 13 pages., 13.
stenutz.eu, "Material Data Sheet for Propylene Glycol", Accessed Sep. 15, 2020.

* cited by examiner

HIGH FREQUENCY POLARIZATION AEROSOL GENERATOR

TECHNICAL FIELD

The present invention relates generally to electronic smoking devices, electronic cigarettes, and similar vaporizing devices and methods.

BACKGROUND

An electronic smoking device, such as an electronic cigarette (e-cigarette), typically has a housing accommodating an electric power source (e.g. a single use or rechargeable battery, electrical plug, or other power source), and an electrically operable atomizer. The atomizer vaporizes liquid supplied from a reservoir and converts liquid into a vapor or aerosol. Control electronics control the activation of the atomizer. In some devices, an airflow sensor is provided to detect a user puffing on the device (e.g., by sensing an under-pressure or an air flow pattern through the device). The airflow sensor signals the puff to the control electronics to power up the device and generate vapor. In other devices, a switch is used to switch on the electrically operable atomizer. These types of devices are collectively referred to here as e-cigarettes, although they may be sized and shaped unlike a conventional tobacco cigarette.

The electrically operable atomizers often use a resistance heater to heat the liquid. Resistance heaters in the form of a wire coil have been widely used in many e-cigarette designs. Ceramic plate heaters and solid heater rods have also been proposed. While these and others have been successfully used in the past, they also present performance considerations including, depending on the specific design, corrosion or build-up of residue on the heating element, short and long term changes in electrical resistance, and other factors which may affect the generation of vapor. Accordingly, engineering challenges remain in the design of e-cigarettes and specifically in the design of atomizers as used in e-cigarettes.

SUMMARY

In one aspect of the present invention, a vaporizing device includes a housing containing an electrical power source such as a battery electrically connected to a high frequency oscillation circuit. First and second conductors are electrically connected to the high frequency oscillation circuit, with a liquid space between the first and second conductors. A liquid supply in the housing is positioned to provide a liquid into the liquid space. A switch is electrically connected to the high frequency oscillation circuit for turning on the high frequency oscillation circuit to vaporize the liquid via dielectric heating. The switch may be provided as an inhalation sensor connected to an electronic controller. The liquid space may be planar or annular, and dimensioned to allow liquid to flow into the liquid space via capillary forces.

In a method of use, a polar liquid is supplied to a space between first and second conductors connected to an oscillating high frequency source. Molecules of the polar liquid are vibrated at high frequency via the oscillating electric field created between the first and second conductors. The vibration generates heat within the liquid causing the liquid to change into vapor. The polar liquid may include nicotine or other physiologically active substance, which is contained in the vapor and inhaled by a user.

The characteristics, features and advantages of this invention and the manner in which they are obtained will become more apparent and be more clearly understood in connection with the following description of exemplary embodiments, which are explained with reference to the accompanying drawings.

BRIEF DESCRIPTION OF THE DRAWINGS

In the drawings, the same element number indicates the same element in each of the views.

FIG. 1 is a schematic cross-sectional illustration of an exemplary e-cigarette.

FIG. 2 is a schematic of inductance coupling oscillation voltage boost circuit FIG. 3 is a schematic of capacitor oscillation circuit.

FIG. 4 is a schematic of transformer oscillation circuit.

FIG. 5 is a schematic of push-pull type oscillation circuit.

FIG. 6 is a schematic of MOSFET push-pull type oscillation circuit.

FIG. 7 is a section view of electrode pads of the atomizer shown in FIG. 1.

FIG. 8 is a section view of electrode pads with a liquid conductor or wick.

FIG. 9 is a top view of a mesh electrode pad.

FIG. 10 is a section view of tube type electrode pad.

FIG. 11 is a diagram of voltage boost before the oscillation circuit.

FIG. 12 is a diagram of voltage boost after the oscillation circuit.

DETAILED DESCRIPTION

As is shown in FIG. 1, an e-cigarette 10 typically has a housing 11 having a cylindrical hollow tube which may be single piece or a multiple piece tube. In FIG. 1, the cylindrical hollow tube is shown as a two piece structure having a battery section 12 and an atomizer/liquid reservoir section 14. Together the battery section 12 and the atomizer/liquid reservoir section 14 form a device which is approximately the same size and shape as a conventional cigarette, typically about 100 mm with a 7.5 mm diameter, although lengths may range from 70 to 150 or 180 mm, and diameters from 5 to 20 mm.

The battery section 12 and the atomizer/liquid reservoir section 14 are typically made of metal or plastic and act together with end caps provide a housing to contain the operative elements of the e-cigarette 10. The battery section 12 and a atomizer/liquid reservoir section 14 may be configured to fit together by a friction push fit, a snap fit, or a bayonet attachment, magnetic fit, or screw threads. An end cap 16 is provided at the front end of the battery section 12. The end cap 16 may be translucent to allow an LED 20 positioned near the end cap to emit light through the end cap. Alternatively the end cap may be opaque and the LED omitted.

An air inlet 38 may be provided in the end cap, at the edge of the inlet next to the cylindrical hollow tube, anywhere along the length of the cylindrical hollow tube, or at the connection of the battery section 12 and the atomizer/liquid reservoir section 14. FIG. 1 shows a pair of air inlets 38 provided at the intersection between the battery section 12 and the atomizer/liquid reservoir section 14. An air outlet 40 is provided at the back end of the atomizer/liquid reservoir section 14 remote from the end cap 16. The air outlet 40 may be formed in the atomizer/liquid reservoir section 14 or it may be formed in a separate end cap or mouthpiece.

A battery 18, the LED 20, control electronics 22 and optionally an airflow sensor 24 are provided within the battery section 12. The battery 18 is electrically connected to the control electronics 22, which is electrically connected to the LED 20 and the airflow sensor 24. In this example the LED 20 is at the front end of the battery section 12, adjacent to the end cap 16 and the control electronics 22 and airflow sensor 24 are provided in the central cavity at the other end of the battery 18 adjacent the atomizer/liquid reservoir section 14. The control electronics 22 may include a programmable microprocessor.

The airflow sensor 24 acts as a puff detector, detecting a user inhaling or sucking on the outlet 40. The airflow sensor 24 can be any suitable sensor for detecting changes in airflow or air pressure such a microphone switch including a deformable membrane which is caused to move by variations in air pressure. Alternatively the sensor may be a Hall element or an electro-mechanical sensor.

The control electronics 22 are also connected to an atomizer 26 provided in the atomizer/liquid reservoir section 14. A central passage 32 may be surrounded by a cylindrical liquid supply 34 with a supply tube or wick 30 abutting or extending into the liquid supply 34. The wick 30 may be a porous material such as a bundle of fiberglass fibers, with liquid 36 in the liquid supply 34 drawn by capillary action through the wick to the atomizer 26.

The liquid supply 34 may be a flex wall or rigid wall bottle or container holding bulk liquid or alternatively it may include wadding soaked in liquid which encircles the central passage 32 with the ends of the wick 30 abutting the wadding. The liquid supply 34 may optionally be provided as a toroidal cavity arranged to be filled with liquid and with the ends of the wick 30 extending into the toroidal cavity.

Where the liquid is polar, or is otherwise subject to dielectric heating, the atomizer 26 may operate by vibrating the molecules of liquid via a high frequency electric field (AC). This vibration generates heat in the liquid, changing the liquid into vapor. The heat is generated inside the liquid. Consequently, there is no transferring of heat from a heating element, such as a resistance coil, into the liquid. Overheating and degradation are avoided. The liquid may include propylene glycol, glycerol or glycerin, and have a dipole moment of 1.0 to 8.0 Debyes.

The atomizer 26 may be provided as first and second electrodes or electrode pads or plates 56 electrically connected to a high frequency oscillation circuit 50, with a liquid space 70 between the pads 56. The electrode pads 56 are electrically conducting, and may be metal, with or without a non-conducting protective film or layer. The electrode pads 56 can have various shapes, such as flat and round, triangular, square, tooth-like or rectangular. The dimension DD of the open space between the electrode pads 56 forming the liquid space 70 may be selected so that liquid is drawn into the liquid space 70 via capillary action. This dimension DD will vary depending on the characteristics of the liquid and may typically range from 0.5 to 4 mm. Where flat electrode pads 56 are used, they are generally aligned and parallel to each other.

Figure 9:
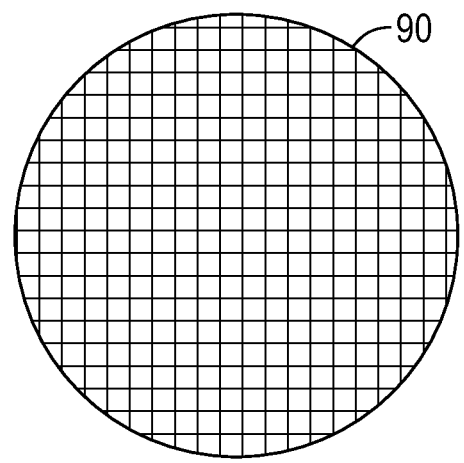
Figure 10:
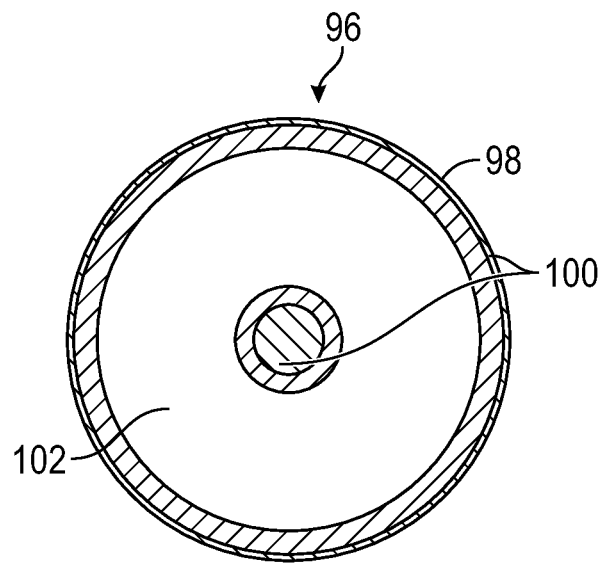

FIG. 9 shows a wire or metal mesh electrode pad 90 which may be used in place of solid pads. FIG. 10 shows a tubular atomizer 96 having a tubular or cylindrical heat insulation layer 98, a metal conductor or other conductive layer 100, and porous material or fiber layer 102.

Figure 2:
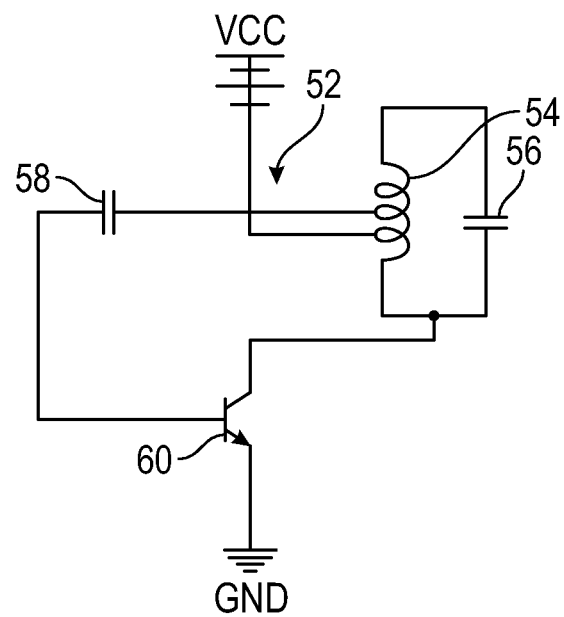

FIG. 2 shows a high frequency oscillation circuit 50, in this case provided as an inductance coupling oscillation circuit 52. An inductor 54 and electrode pads 56 form an LC basic oscillation loop. A capacitor 58 provides a positive feedback signal and a transistor 60 forms the oscillation circuit. Liquid 36 between the electrode pads 56 undergoes dielectric heating to create a vapor.

Figure 3:
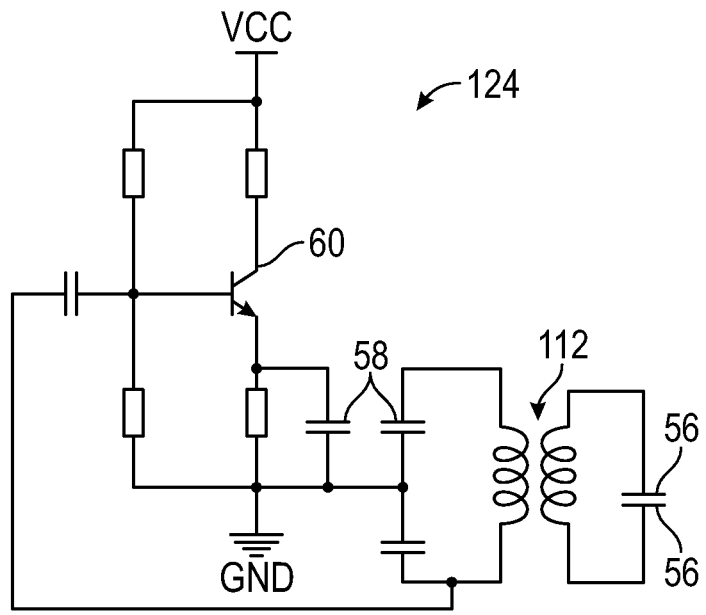
Figure 6:
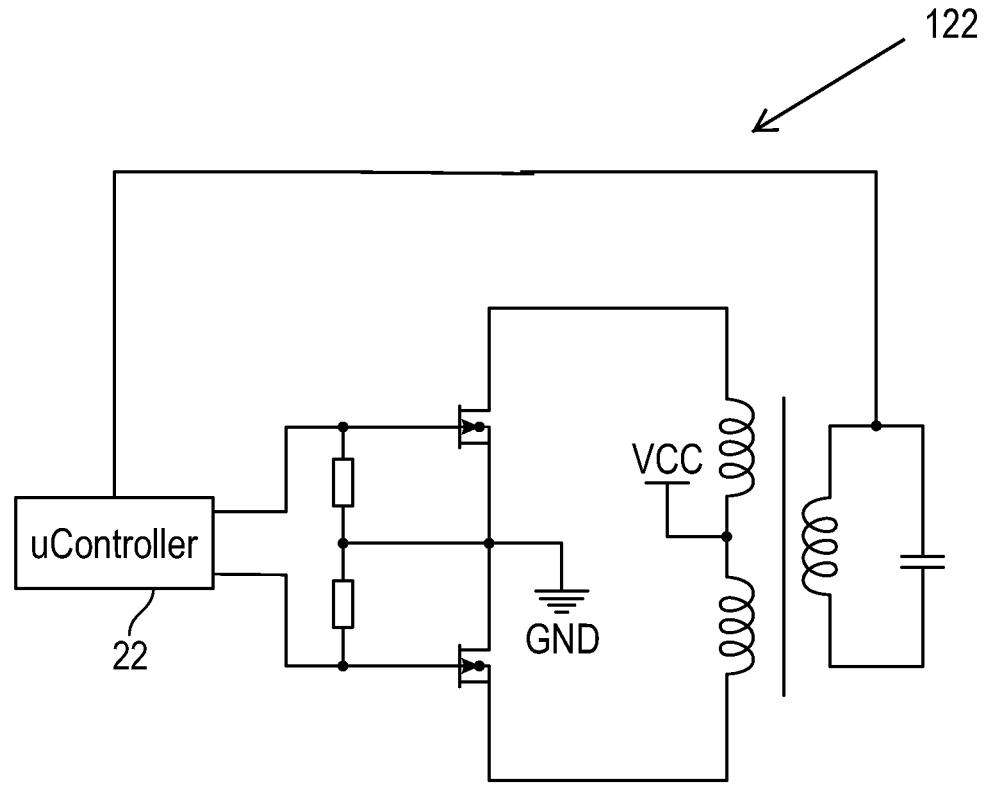

The vapor is entrained air flow through the housing 11 and cools and condenses to form an aerosol. FIG. 3 shows a capacitor isolation circuit 124 with a transformer 112 isolated via capacitors 58, FIG. 6 shows a MOSFET push-pull type oscillation circuit 122 which may also be used.

Figure 7:
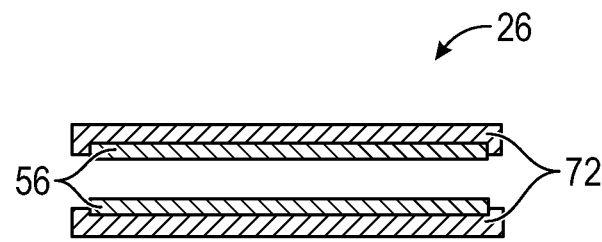

Referring to FIG. 7, a thermal insulator or insulation layer 72 may be provided on the back and/or the sides of the electrode pads 56. The insulation layer 72 may be an open space or gap filled with air and/or aerosol, porous material, or fiber material. The electrode pad material preferably combines both heat insulation and electrical conductivity. Carbon aerogel may be used as the electrode pad material.

Figure 8:
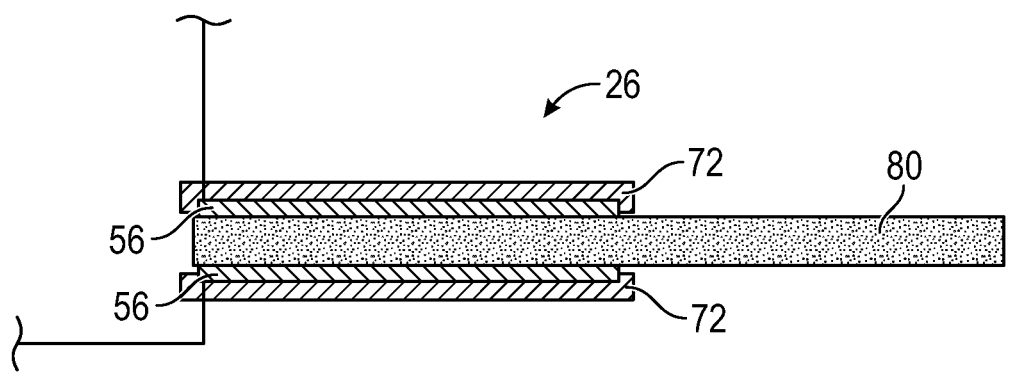

Turning to FIG. 8, a liquid conductor 80 may be used to provide a continuous supply of liquid to the atomizer 26. The liquid conductor 80 may be a porous material extending between the two electrode pads 56.

Figure 11:
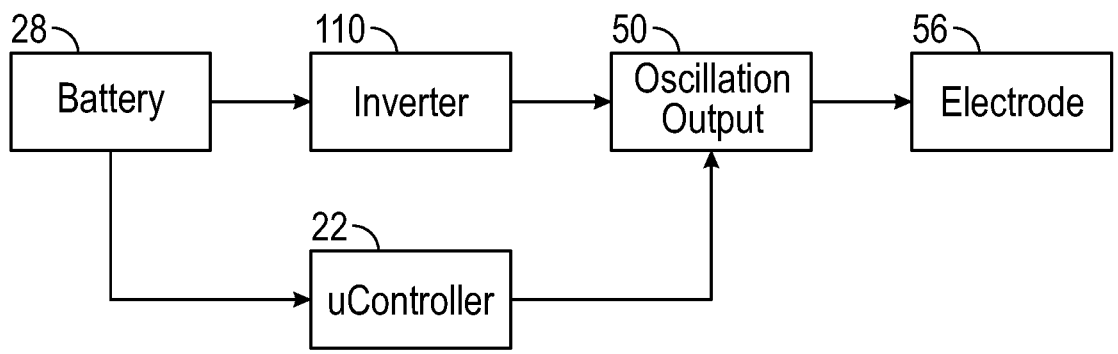
Figure 12:
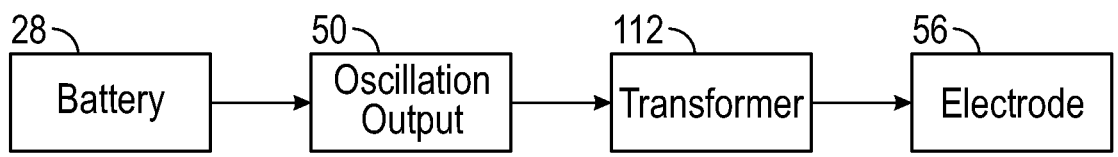

The nominal voltage of the battery 18 (typically 1-12 V DC) may be increased using various techniques. FIG. 11 shows an inverter 110 inverting the low battery DC voltage via an inverter to a high voltage and then oscillating to provide a high frequency oscillation voltage to the atomizer 26. FIG. 12 shows a design with the oscillation circuit 50 generating a high frequency AC voltage output with a transformer 112 increasing the AC voltage which is then applied to the electrode pads 56. Alternatively, an inverter 110 may be used to increase the DC voltage to drive the oscillation circuit 50, with a transformer 112 used to increase the AC voltage applied to electrode pads 56.

Figure 4:
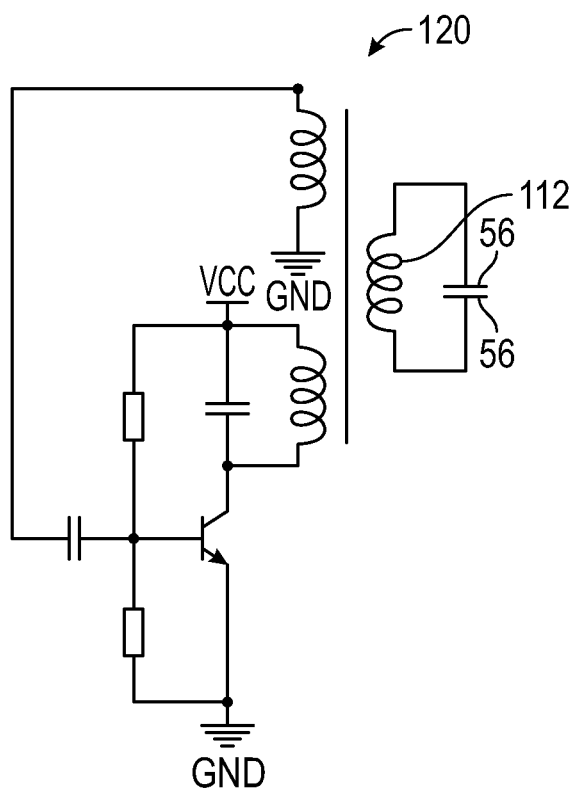
Figure 5:
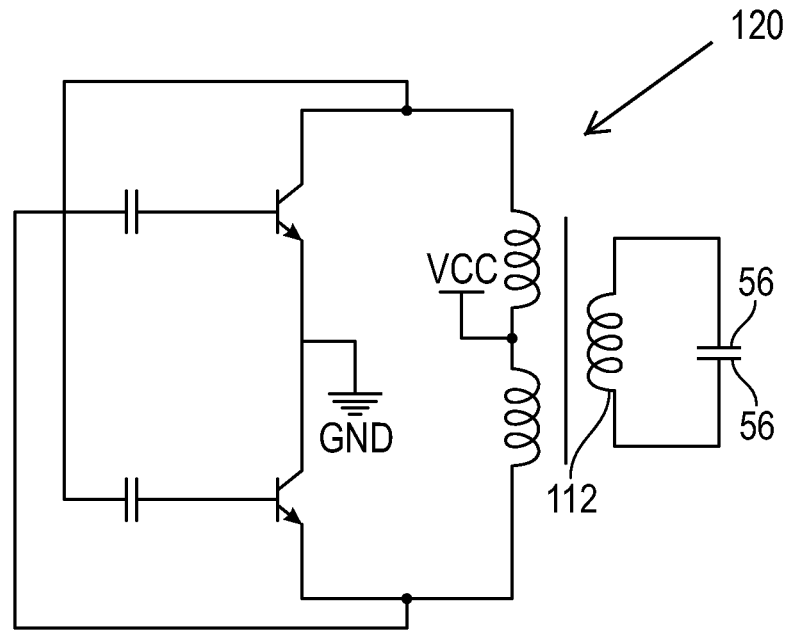

High frequency voltage can be generated from a transformer isolation circuit 118 as shown in FIG. 4, a push-pull oscillator 120, as shown in FIG. 5, or via a MOSFET push-pull oscillation circuit 122 as shown in FIG. 6, with the oscillator output connected to the electrode pads 56. The high frequency oscillation circuit may operate at 50 KHz to 980 MHz and at 30 volts to 5000 volts. Different liquid compositions will vaporize efficiently using frequency and voltage combinations within these ranges.

In use, a user inhales on the outlet 40 causing air to be drawn into the housing 11 via the air inlet 38 and through the central passage 32. The resulting change in air pressure is detected by the airflow sensor 24 (if used) which generates an electrical signal that is passed to the control electronics 22. In response to the signal, the control electronics 22 activates the atomizer 26 which causes liquid 36 in the liquid space 70 to be vaporized via dielectric heating creating an aerosol (which may include gaseous and liquid components) within the central passage 32. Where the liquid has polar molecules, such as water or glycol, or if the liquid has weakly bonded molecules, the molecules tend to orient into alignment with oscillating electric field, causing molecular dipole rotation, which can quickly heat the liquid via dielectric heating.

As the user continues to inhale, the vapor is drawn through the central passage 32 and inhaled by the user. At the same time the control electronics 22 may activate the LED 20 (if used) causing the LED 20 to light up and create light which is visible via the translucent end cap 16 simulating the appearance of a glowing ember at the end of a conventional cigarette. As liquid present in the wick 30 is converted into an aerosol more liquid is drawn into the wick 30 from the liquid supply 34 by capillary action and moved to the atomizer 26.

Some e-cigarette are intended to be disposable and the electric power of the battery 18 is intended to be sufficient to vaporize the liquid contained within the liquid supply 34 after which the e-cigarette 10 is thrown away. In other embodiments the battery 18 is rechargeable and the liquid supply is refillable. In the cases where the liquid supply 34 is a toroidal cavity, this may be achieved by refilling the liquid supply via a refill port. The atomizer/liquid reservoir section 14 may be detachable from the battery section 12 and a new atomizer/liquid reservoir section 14 can be fitted with a new liquid supply 34 thereby replenishing the supply of liquid. In some cases, replacing the liquid supply 34 may involve replacement of the atomizer 26 and the wick 30 along with the replacement of the liquid supply 34.

The new liquid supply 34 may be in the form of a cartridge, optionally having the central passage 32 through which a user inhales aerosol. Rather than inhaling aerosol via a central passage 32, the cartridge may block the central section of the e-cigarette 10 and generated aerosol may be directed around the exterior of the cartridge to the outlet 40 for inhalation.

Of course, in addition to the above description of the structure and function of a typical e-cigarette 10, variations also exist. For example, the LED 20 may be omitted. The airflow sensor 24 may be placed adjacent the end cap 16 rather than in the middle of the e-cigarette. The airflow sensor 24 may be replaced with a switch which enables a user to activate the e-cigarette manually rather than in response to the detection of a change in air flow or air pressure.

Thus, novel designs have been shown and described. Various changes and substitutions may of course be made without departing from the spirit and scope of the invention. The invention, therefore, should not be limited, except by the following claims and their equivalents.

The invention claimed is:

1. A high frequency polarization aerosol generator, comprising:
- a battery section containing a battery electrically connected to a high frequency oscillation circuit including an inductance coupling oscillation voltage boost circuit including an inductor, and operating at a frequency of 50 KHz to 980 MHz and at a voltage of 30 to 5000 V;
- an atomizer section attachable to and detachable from the battery section;
- a dielectric heater in the atomizer section, the dielectric heater including first and second flat and parallel electrode pads electrically connected to the high frequency oscillation circuit, the first and second electrode pads and the inductor forming an LC oscillation loop;
- a space for liquid between the first and second electrode pads;
- a liquid supply in the atomizer section positioned to provide a polar liquid into the space for liquid, with the liquid contacting the first and second electrode pads;
- the dielectric heater in a central passage through the atomizer section, the dielectric heater surrounded by the liquid supply; and
- a switch or a sensor electrically connected to the high frequency oscillation circuit for turning on the high frequency oscillation circuit to vaporize the liquid in the space for liquid via dielectric heating.

2. The high frequency polarization aerosol generator of claim 1 wherein the high frequency oscillation circuit includes a capacitor for providing a positive feedback signal.

3. The high frequency polarization aerosol generator of claim 1, further comprising an inverter adapted for inverting DC voltage from the battery to drive the oscillation circuit with a transformer used to increase AC voltage applied to the first and second electrode pads.

4. The high frequency polarization aerosol generator of claim 1 further including an inverter adapted for inverting DC voltage from the battery to drive the high frequency oscillation circuit.

5. The aerosol generator of claim 1 wherein the polar liquid is drawn into the space for liquid between the first and second electrode pads via capillary action.

6. A high frequency polarization aerosol generator, comprising:
- a battery section containing a battery electrically connected to a high frequency oscillation circuit;
- an atomizer section attachable to and detachable from the battery section;
- a dielectric heater in the atomizer section, the dielectric heater including first and second electrode pads electrically connected to the high frequency oscillation circuit;
- a space for liquid between the first and second electrode pads;
- a liquid supply in the atomizer section housing positioned to provide a polar liquid into the space for liquid; the dielectric heater in a central passage through the atomizer section, the dielectric heater surrounded by the liquid supply; and
- a switch or a sensor electrically connected to the high frequency oscillation circuit for turning on the high frequency oscillation circuit to vaporize the liquid in the space for liquid via dielectric heating.

7. The aerosol generator of claim 6 wherein the high frequency oscillation circuit operates at a frequency of 50 KHz to 980 MHz and at a voltage of 30 to 5000 V.

8. The aerosol generator of claim 7 wherein the first and second electrode pads are flat and parallel to each other.

9. The aerosol generator of claim 8 wherein the polar liquid is drawn into the space for liquid between the first and second electrode pads via capillary action.

10. The aerosol generator of claim 8 wherein the first and second electrode pads are spaced apart by 0.5 to 4 mm.

11. The aerosol generator of claim 10 wherein the polar liquid contacts the first and second electrode pads.

12. A high frequency polarization aerosol generator, comprising:
- a battery section containing a battery electrically connected to a high frequency oscillation circuit operating at a frequency of 50 KHz to 980 MHz and at a voltage of 30 to 5000 V;
- an atomizer section attachable to and detachable from the battery section;
- a dielectric heater in the atomizer section, the dielectric heater including first and second flat, spaced apart, and parallel electrode pads electrically connected to the high frequency oscillation circuit;
- a liquid supply in the atomizer section positioned to provide a polar liquid into a space between the electrode pads with the liquid contacting the electrode pads;
- the dielectric heater in a central passage through the atomizer section, the dielectric heater surrounded by the liquid supply; and
- a sensor electrically connected to the high frequency oscillation circuit for turning on the high frequency oscillation circuit to vaporize the liquid via dielectric heating.

13. The aerosol generator of claim 12 wherein the polar liquid is drawn between the first and second electrode pads via capillary action.

* * * * *